US 9,320,504 B2

(12) United States Patent
Wilson et al.

(10) Patent No.: US 9,320,504 B2
(45) Date of Patent: Apr. 26, 2016

(54) DEVICES, SYSTEMS, AND METHODS FOR CONTROLLED HYDRODISSECTION OF VESSEL WALLS

(71) Applicant: InterVene, Inc., Mountain View, CA (US)

(72) Inventors: Fletcher T. Wilson, San Francisco, CA (US); David Batten, San Jose, CA (US); Zachary J. Malchano, San Francisco, CA (US); Antonio Rosales, Oslo (NO); Eivind Osnes, Oslo (NO)

(73) Assignee: INTERVENE, INC., Mountain View, CA (US)

(*) Notice: Subject to any disclaimer, the term of this patent is extended or adjusted under 35 U.S.C. 154(b) by 0 days.

(21) Appl. No.: 14/667,670

(22) Filed: Mar. 24, 2015

(65) Prior Publication Data
US 2015/0265302 A1    Sep. 24, 2015

Related U.S. Application Data

(60) Provisional application No. 61/969,263, filed on Mar. 24, 2014, provisional application No. 61/969,262, filed on Mar. 24, 2014.

(51) Int. Cl.
*A61B 17/3203*    (2006.01)
*A61B 17/00*    (2006.01)
(Continued)

(52) U.S. Cl.
CPC ......... *A61B 17/00234* (2013.01); *A61B 5/0066* (2013.01); *A61B 5/0084* (2013.01);
(Continued)

(58) Field of Classification Search
CPC ........... A61B 17/3203; A61B 17/3207; A61B 17/32037; A61B 19/24

USPC .......................................... 606/159, 167, 170
See application file for complete search history.

(56) References Cited

U.S. PATENT DOCUMENTS 5,464,395 A    11/1995    Faxon et al.
5,601,588 A    2/1997    Tonomura et al.
(Continued)

FOREIGN PATENT DOCUMENTS

CA    2678971    8/2008
RU    2160057    12/2000
(Continued)

OTHER PUBLICATIONS

Corcos, I., "A new autologous venous valve by intimal flap: One cases report." Note Di Tecnica, Minerva Cardioangiol, 2003, 51, 10 pages.

(Continued)

*Primary Examiner* — Kathleen Holwerda
(74) *Attorney, Agent, or Firm* — Perkins Coie LLP

(57) ABSTRACT

A device and method for intravascular dissection of a body lumen, and particularly a blood vessel wall, is disclosed herein. One aspect of the present technology, for example, is directed toward a tubular elongated member having a lumen therethrough, wherein the elongated member includes a distal region configured to be positioned within a blood vessel wall. The distal region can include an angled distal face having a distal-most edge configured to puncture the vessel wall and a proximal-most edge. The member can include an exit port fluidly coupled to the lumen, and positioned along the distal face between the distal-most edge and the proximal-most edge. A central longitudinal axis of the exit port can be offset from a central longitudinal axis of the elongated member such that the exit port is closer to the distal-most edge than the proximal-most edge.

23 Claims, 7 Drawing Sheets

(51) Int. Cl.
*A61B 8/12* (2006.01)
*A61B 5/00* (2006.01)
*A61B 17/12* (2006.01)
*A61B 8/00* (2006.01)
*A61B 17/22* (2006.01)

(52) U.S. Cl.
CPC ............... *A61B 8/12* (2013.01); *A61B 8/4494* (2013.01); *A61B 17/12136* (2013.01); *A61B 17/22* (2013.01); *A61B 17/3203* (2013.01); *A61B 17/32037* (2013.01); *A61B 17/12109* (2013.01); *A61B 2017/00292* (2013.01); *A61B 2017/00778* (2013.01); *A61B 2017/00783* (2013.01); *A61B 2017/22095* (2013.01); *A61B 2090/3735* (2016.02); *A61B 2562/043* (2013.01)

(56) References Cited

U.S. PATENT DOCUMENTS

| | | | |
|---|---|---|---|
| 5,810,847 | A | 9/1998 | Laufer et al. |
| 5,836,945 | A | 11/1998 | Perkins |
| 6,475,226 | B1 | 11/2002 | Belef et al. |
| 6,506,178 | B1 | 1/2003 | Schubart et al. |
| 6,514,217 | B1 | 2/2003 | Selmon et al. |
| 6,685,648 | B2 | 2/2004 | Flaherty et al. |
| 6,902,576 | B2 | 6/2005 | Drasler et al. |
| 7,008,411 | B1 | 3/2006 | Mandrusov et al. |
| 7,179,249 | B2 | 2/2007 | Steward et al. |
| 7,273,469 | B1 | 9/2007 | Chan et al. |
| 7,517,352 | B2 | 4/2009 | Evans et al. |
| 7,918,870 | B2 | 4/2011 | Kugler et al. |
| 7,927,305 | B2 | 4/2011 | Yribarren et al. |
| 7,938,819 | B2 | 5/2011 | Kugler et al. |
| 7,955,346 | B2 | 6/2011 | Mauch et al. |
| 8,025,655 | B2 | 9/2011 | Kugler et al. |
| 8,083,727 | B2 | 12/2011 | Kugler et al. |
| 8,100,860 | B2 | 1/2012 | von Oepen et al. |
| 8,114,123 | B2 | 2/2012 | Brenzel et al. |
| 8,460,316 | B2 | 6/2013 | Wilson et al. |
| 2002/0103459 | A1 | 8/2002 | Sparks et al. |
| 2004/0167558 | A1 | 8/2004 | Igo et al. |
| 2005/0075665 | A1 | 4/2005 | Brenzel et al. |
| 2005/0165466 | A1 | 7/2005 | Morris et al. |
| 2006/0094929 | A1 | 5/2006 | Tronnes |
| 2006/0136045 | A1 | 6/2006 | Flagle et al. |
| 2006/0271090 | A1 | 11/2006 | Shaked et al. |
| 2009/0209910 | A1 | 8/2009 | Kugler et al. |
| 2009/0254051 | A1 | 10/2009 | von Oepen et al. |
| 2010/0152682 | A1 | 6/2010 | Mauch et al. |
| 2010/0152843 | A1 | 6/2010 | Mauch et al. |
| 2010/0256599 | A1 | 10/2010 | Kassab et al. |
| 2011/0264125 | A1* | 10/2011 | Wilson ........... A61B 17/320016 606/159 |
| 2012/0143234 | A1 | 6/2012 | Wilson et al. |
| 2012/0289987 | A1* | 11/2012 | Wilson ........... A61B 17/320016 606/190 |
| 2013/0103070 | A1* | 4/2013 | Kugler ................ A61B 17/221 606/185 |
| 2014/0012301 | A1 | 1/2014 | Wilson et al. |

FOREIGN PATENT DOCUMENTS

| | | |
|---|---|---|
| WO | WO-9900059 | 1/1999 |
| WO | WO-2010074853 | 7/2010 |
| WO | WO-2011106735 | 9/2011 |
| WO | WO-2012145444 | 10/2012 |
| WO | WO-2013119849 | 8/2013 |

OTHER PUBLICATIONS

Final Office Action for U.S. Appl. No. 13/035,752, dated Apr. 4, 2013, 12 pages.
International Search Report & Written Opinion for International Application No. PCT/US12/34138 dated Aug. 10, 2012, 8 pages.
International Search Report and Written Opinion for International App. No. PCT/US2011/026370, Dated Jul. 7, 2011, 10 pages.
International Search Report and Written Opinion for International App. No. PCT/US2013/025196, Mailed Apr. 25, 2013, 7 pages.
International Search Report for International App. No. PCT/US14/011169, dated May 22, 2014, 2 pages.
Lugli, M., et al., Neovalve construction in the deep venous incompetence. J. Vasc. Surg., Jan. 2009, 49(1), 156-62.
Maleti, O., Neovalve construction in postthrombotic syndrome. Journal of Vascular Surgery, vol. 34, No. 4, 6 pages.
Non-Final Office Action for U.S. Appl. No. 13/450,432, Mailed Feb. 19, 2014, 8 pages.
Non-Final Office Action for U.S. Appl. No. 13/035,818 dated Sep. 14, 2012, 7 pages.
Non-Final Office Action for U.S. Appl. No. 13/035,752, Mailed May 19, 2014, 11 pages.
Non-Final Office Action for U.S. Appl. No. 13/035,752, Mailed Oct. 16, 2012, 13 pages.
Notice of Allowance for U.S. Appl. No. 13/035,818 dated Feb. 22, 2013, 7 pages.

* cited by examiner

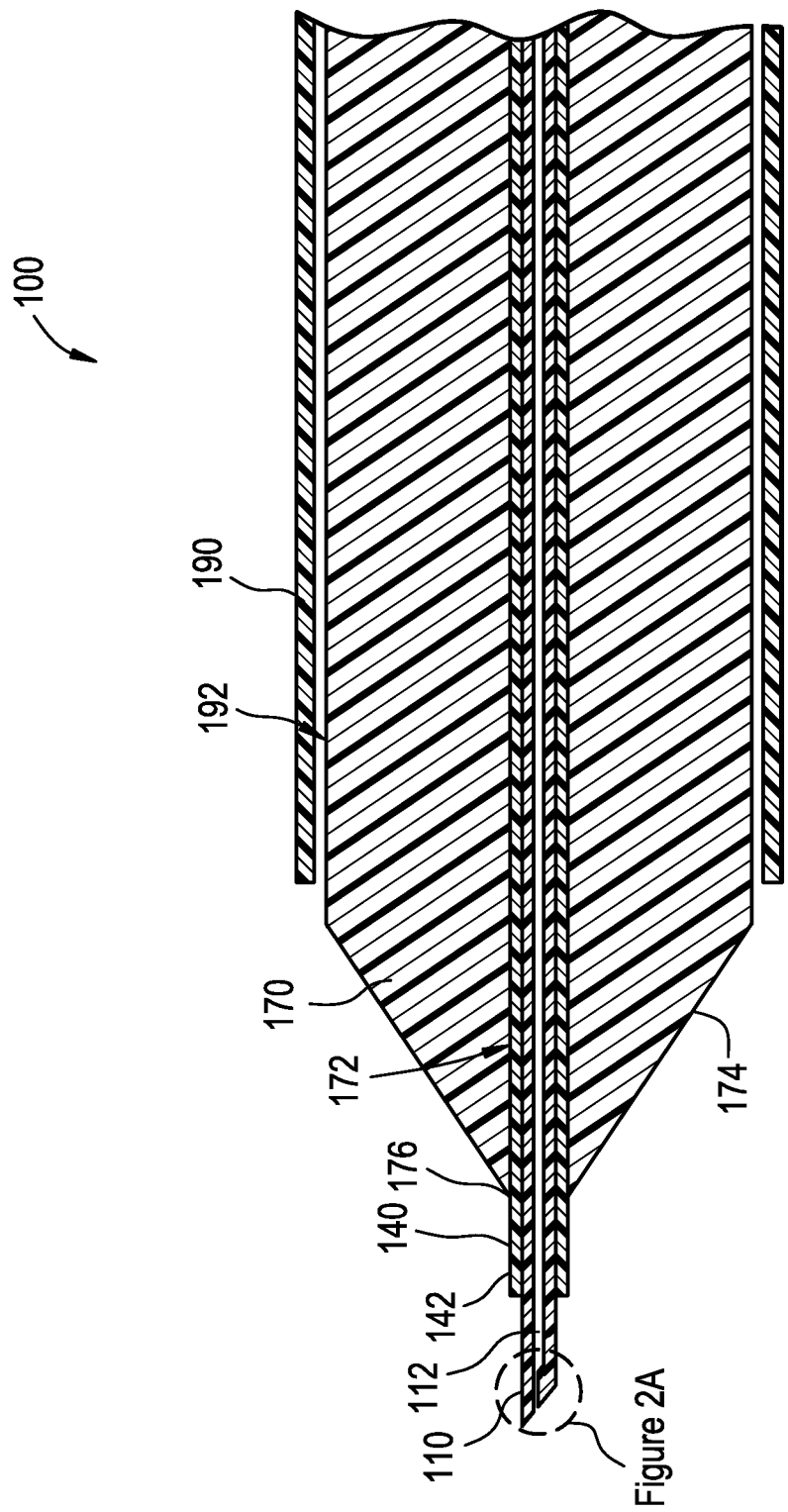

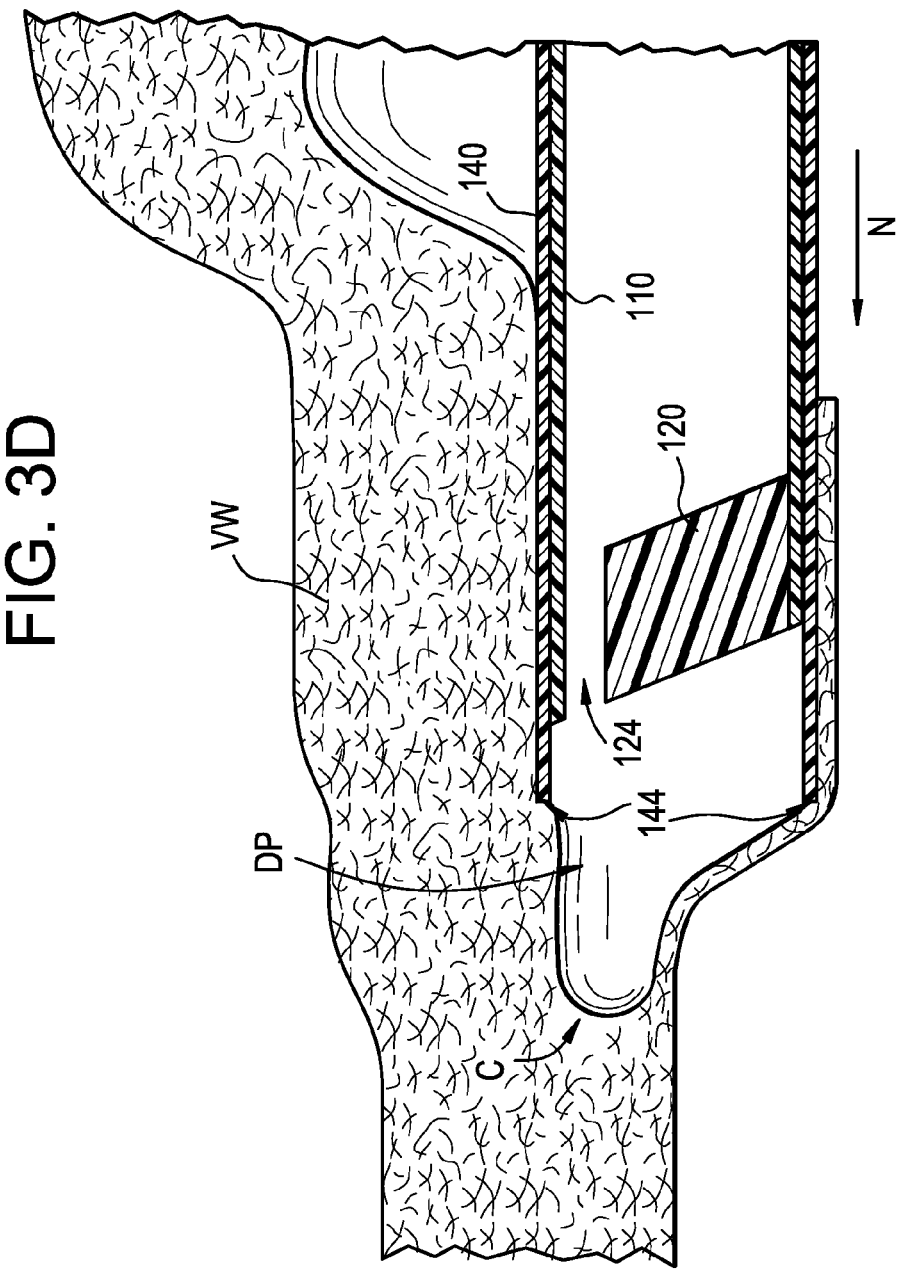

DEVICES, SYSTEMS, AND METHODS FOR CONTROLLED HYDRODISSECTION OF VESSEL WALLS

CROSS-REFERENCE TO RELATED APPLICATION(S)

The present application claims the benefit of U.S. Provisional Application No. 61/969,262, filed Mar. 24, 2014 and U.S. Provisional Application No. 61/969,263, filed Mar. 24, 2014, both of which are incorporated herein by reference in their entireties.

TECHNICAL FIELD

The present technology relates generally to devices and methods for intravascular modification of body lumens. Many embodiments of the present technology relate to devices, systems and methods for controlled dissection of blood vessel walls.

BACKGROUND

Controlled dissection of a body lumen wall is a necessary treatment component of many widespread medical conditions. For example, in order to bypass a chronic total occlusion (CTO) in the vascular system, the physician can use a catheter to enter and travel through a length of the blood vessel wall corresponding to the site of the occlusion. As another example, one course of treatment for venous reflux involves modification of the blood vessel wall to create a valve and/or valve leaflet and/or repair a faulty valve and/or valve leaflet. One method for autologous creation of a valve leaflet, for instance, includes accessing the treatment site (either surgically or intravascularly) and entering the vessel wall with a catheter to create a dissection pocket (e.g., a portion of a body lumen wall where the wall has been separated into two or more distinct layers). Depending on the procedure (e.g., bypassing a CTO, creating a leaflet, etc.), it can be advantageous to finely control the shape and size of the dissection pocket. Such control can be challenging, especially considering the thinness and fragility of most body lumen walls, the presence of pathologic changes to body lumen walls, the curvature of most body lumen walls, and the effects of local, dynamic blood flow. Accordingly, the devices, systems, and methods of the present technology address these challenges.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1 is a cross-sectional side view of a dissection assembly in accordance with an embodiment of the present technology.

FIGS. 3A-3D illustrate a method for using a dissection assembly in accordance with the present technology to dissect a vessel wall.

DETAILED DESCRIPTION

Figure 2A:
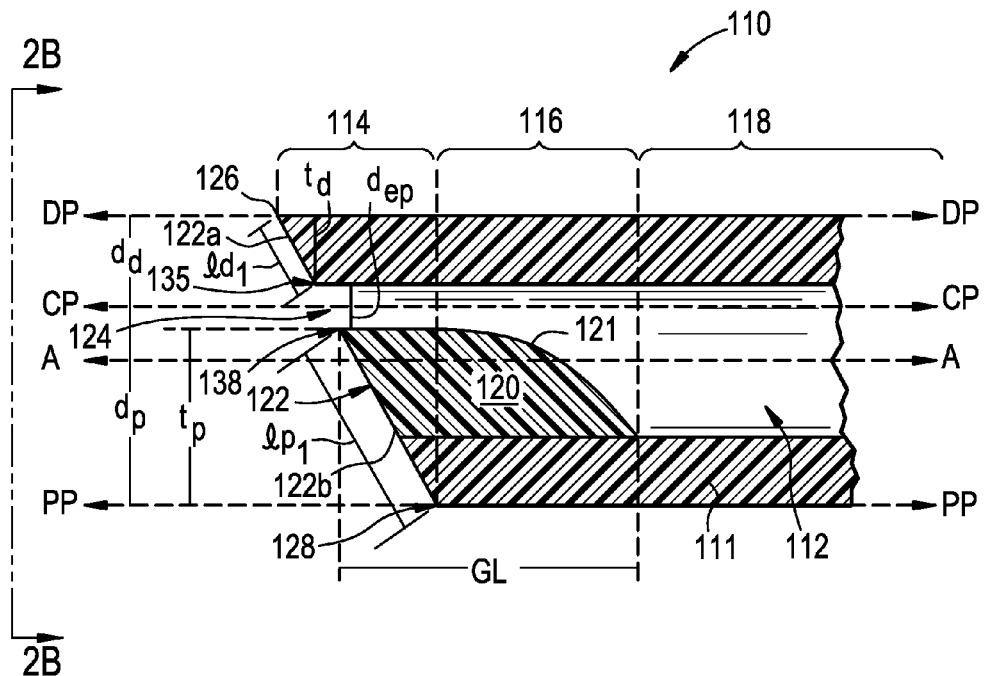
FIG. 2A is an enlarged, isolated, cross-sectional side view of a portion of a dissection assembly in accordance with an embodiment of the present technology.

The present technology provides dissection devices, systems, and methods for intravascular creation of dissection pockets within the wall of a body lumen. Specific details of several embodiments of treatment devices, systems and associated methods in accordance with the present technology are described below with reference to FIGS. 1-3D. Although many of the embodiments are described below with respect to devices, systems, and methods for intravascular creation of autologous venous valves and/or valve leaflets, other applications and other embodiments in addition to those described herein are within the scope of the technology. For example, the devices, systems, and methods of the present technology can be used in any body cavity or lumen or walls thereof (e.g., arterial blood vessels, venous blood vessels, urological lumens, gastrointestinal lumens, etc.) and used for surgical creation of autologous valves, for repair of autologous and/or synthetic valves, as well as for sub-intimally traversing chronic total occlusions. Additionally, several other embodiments of the technology can have different states, components, or procedures than those described herein. Moreover, it will be appreciated that specific elements, substructures, advantages, uses, and/or other features of the embodiments described with reference to FIGS. 1-3D can be suitably interchanged, substituted or otherwise configured with one another in accordance with additional embodiments of the present technology.

Furthermore, suitable elements of the embodiments described with reference to FIGS. 1-3D can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-3D. For example, the devices, systems, and methods of the present technology can be used with any of the catheter devices, systems, and methods disclosed in U.S. patent application Ser. No. 13/035,752, filed Feb. 2, 2011; U.S. patent application Ser. No. 13/035,818, filed Feb. 25, 2011; U.S. patent application Ser. No. 13/450,432, filed Apr. 18, 2012; U.S. Provisional Patent Application No. 61/969,262, filed Mar. 24, 2013; U.S. Provisional Patent Application No. 61/969,263, filed Mar. 24, 2013; U.S. patent application Ser. No. 13/926,886, filed Jun. 25, 2013; PCT Application No. PCT/US2014/011169, filed Jan. 10, 2014; U.S. patent application Ser. No. 14/377,492, filed Aug. 7, 2014; U.S. patent application Ser. No. 14/498,969, filed Sep. 26, 2014; and U.S. Provisional Patent Application No. 62/092,809, filed Dec. 16, 2014, all of which are incorporated by reference herein in their entireties (referred to collectively as "the Patents").

With regard to the terms "distal" and "proximal" within this description, unless otherwise specified, the terms can reference a relative position of the portions of a dissection assembly and/or an associated delivery catheter with reference to an operator and/or a location in the vasculature.

I. Selected Embodiments of Dissection Assemblies and Associated Devices

FIG. 1 is a cross-sectional side view of a dissection assembly 100 (or "the assembly 100") in accordance with an embodiment of the present technology for dissecting or otherwise separating two or more portions of a blood vessel wall. As used herein, the term "separating two or more portions of a blood vessel wall" refers to the act of separating the vessel wall at least into a first layer and a second layer. The first layer can include intimal, medial, and/or adventitial tissue, and the second layer can include intimal, medial, and/or adventitial tissue. For example, dissection devices of the present technology can separate an intimal layer from a medial layer, a medial layer from an adventitial layer, a sub-medial layer from a sub-medial layer, an intimal and sub-medial layer from a sub-medial layer, etc.

The dissection assembly 100 can include an inner member 110, an inner sheath 140, an outer member 170, and an outer sheath 190. The inner member 110 can be slidably disposed within a lumen 142 of the inner sheath 140, the inner sheath 140 can be slidably disposed within a lumen 172 of the outer member 170, and the outer member 170 can be slidably disposed within a lumen 192 of the outer sheath 190. In some embodiments, the dissection assembly 100 does not include an outer sheath 190. In a particular embodiment, the dissection assembly 100 does not include an inner sheath 140. In some embodiments, the dissection assembly 100 can include a guidewire (not shown). In such embodiments, for example, the guidewire can be slidably disposed within a lumen 112 of the inner member 110.

The outer sheath 190 can be configured to be slidably received by a delivery catheter, such as any of the delivery catheter embodiments described in one or more of the Patents incorporated by reference herein. One exemplary delivery catheter embodiment is described below with reference to FIGS. 3A-3D. In some embodiments the outer sheath 190 can be a solid tube made of a polymer and/or a metal, and in some embodiments the outer sheath 190 can have a mesh or braided construction and/or can have one or more portions that are stented, braided, slotted, coiled, etc. The thickness of the wall along the distal portion of the outer sheath 190 can be less than the thickness of the wall along a proximal portion of the outer sheath 190. In other embodiments, the outer sheath 190 wall thickness generally does not vary along its length. Additionally, one or more portions of the outer sheath 190 and/or the entire length of the outer sheath 190 can include multiple layers to increase the strength and pushability of the assembly 100. In those embodiments having varying thicknesses along the length of the outer sheath 190, one or more portions of the outer sheath can be tapered so that the outer sheath 190 can more easily dilate or advance into narrow or tight passages, ostia, dissection planes, and/or vessel wall openings.

The outer member 170 can have a tapered distal portion 174. The lumen 172 of the outer member 170 can extend distally from a proximal portion of the outer member 170 to an exit port 176. The outer member 170 can serve at least two functions during tissue dissection. First, the size and shape of the outer member 170 can help position the inner member 110 and the inner sheath 140 such that the inner member 110 and inner sheath 140 exit through the exit port 176 at a predetermined height relative to the delivery catheter lumen (and thus relative to the vessel wall, as described in greater detail below with respect to FIGS. 3A-3D). Second, the tapered shape and relatively high stiffness and/or hardness, among other material properties, of the outer member 170 enable the outer member 170 to dilate soft tissue upon engaging an opening in the tissue.

Figure 2B:
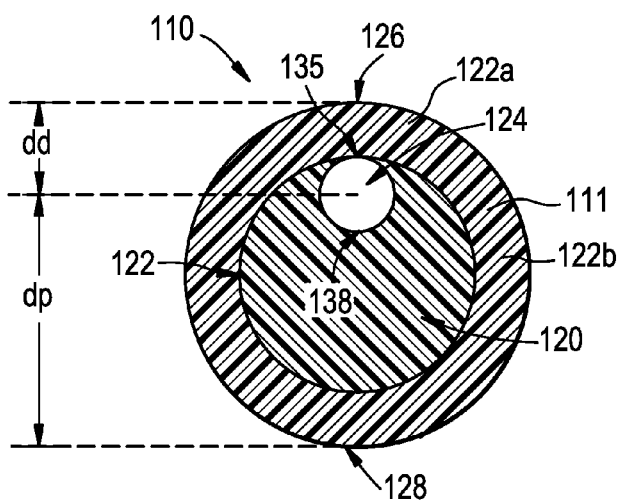
FIG. 2B is an end view of the portion of a dissection assembly shown in FIG. 2A.

FIG. 2A is an isolated, enlarged cross-sectional side view of a distal portion of the inner member 110, and FIG. 2B is an end view taken along line 2B-2B in FIG. 2A. The inner member 110 is configured to puncture the vessel wall (not shown) and be advanced within the vessel wall while ejecting fluid to separate vessel wall tissue, thereby forming a dissection pocket within the vessel wall. As used herein, the term "puncture" refers to an action that gains entry to an interior portion of the vessel wall without crossing through the entire thickness of the vessel wall. Referring to FIGS. 2A-2B together, the inner member 110 can have a tubular wall 111 with an inner surface that defines a lumen 112, a beveled or slanted distal face 122, and an exit port 124 positioned along the distal face 122. The lumen 112 is configured to receive a fluid therethrough and can have a proximal portion (not shown) coupled to a pressurized fluid source (e.g., a syringe, a pump, a mechanical fluid pressurizer, etc.). The lumen 112 extends distally from the proximal portion to the exit port 124, and the inner member 110 is configured to eject the fluid through the exit port 124. The wall 111 can extend distally from the proximal portion of the inner member 110 to the distal face 122. The distal face 122 can have a distal-most edge 126 (shared with a distal terminus of the wall 111) configured to puncture a vessel wall, and a proximal-most edge 128. As shown in FIGS. 2A-2B, the distal-most edge 126 and the proximal-most edge 128 can be positioned opposite one another about a circumference of the inner member 110. In other embodiments, the distal-most edge 126 and the proximal-most edge 128 can have other arrangements.

The exit port 124 can have a distal-most edge 135 and a proximal-most edge 138, and can be offset from a longitudinal axis A of the inner member 110. For example, as shown in FIGS. 2A-2B, a central longitudinal axis CP of the exit port 124 is offset from a central longitudinal axis A of the inner member 110 such that the exit port 124 is positioned along the distal face 122 closer to the distal-most edge 126 than the proximal-most edge 128. Likewise, a distal perpendicular distance $d_d$ (measured between the central longitudinal axis CP of the exit port 124 and a distal longitudinal axis DP running through the distal-most edge 126 of the distal face 122) can be less than a proximal perpendicular distance $d_p$ (measured between the central longitudinal axis CP of the exit port 124 and a proximal longitudinal axis PP running through the proximal-most edge 128 of the distal face 122). In some embodiments, the distal distance $d_d$ can be between about 0.004 inches and about 0.007 inches (e.g., 0.006 inches), and the proximal distance $d_p$ can be between about 0.013 inches and about 0.015 inches (e.g., 0.014 inches). In a particular embodiment, the ratio of the distal distance $d_d$ to the proximal distance $d_p$ can be between about 30% and 50% (e.g., 32%, 36%, 41%, 47%, 48%, etc.). In a particular embodiment, the ratio is between about 30% and about 45% (e.g., 42%, 43%, 44%, etc.)

A portion of the wall 111 extending between the distal-most edge 126 of the distal face and the distal-most edge 135 of the exit port 124 can have a thickness $t_d$ of about 0.001 inches to about 0.003 inches (e.g., about 0.0015 inches, about 0.002 inches, about 0.0023 inches, etc.). The exit port 124 can have an exit port diameter $d_{ep}$ between about 0.002 inches and about 0.012 inches (e.g., 0.003 inches, 0.0042 inches, 0.0059 inches, 0.006 inches, 0.0073 inches, 0.008 inches, 0.009 inches, etc.). A portion of the wall 111 extending between the proximal-most edge 138 of the exit port 124 and the proximal-most edge 128 of the distal face 122 can have a thickness $t_p$ between about 0.008 inches to about 0.012 inches (e.g., about 0.0084 inches, about 0.010 inches, etc.).

As shown in FIGS. 2A-2B, the distal face 122 can have a distal portion 122a and a proximal portion 122b. The distal portion 122a can extend between the distal-most edge 126 of the distal face 122 and the distal-most edge 135 of the exit port 124, and the proximal portion 122b can extend between the proximal-most edge 138 of the exit port 124 and the proximal-most edge 128 of the distal face 122. A length $l_{pl}$ of the proximal portion 122b can be greater than a length $l_{dl}$ of the distal portion 122a, resulting in the exit port 124 being offset along the length of the distal face 122. In some embodiments, the length $l_{pl}$ is one to three times as long as the length $l_{dl}$, and in some embodiments, the length $l_{pl}$ is 1.5 to 2.5 times as long as the length $l_{dl}$. As such, the entire exit port 124 is positioned nearer the puncturing edge 126 of the inner member 110 to provide greater control over tissue dissection, as described in greater detail below with respect to FIGS. 3A-3D.

In some embodiments, the inner member 110 can include a guide-member 120 positioned within the lumen 112 along all or a portion of its length. The guide-member 120 can have a curved, ramped, proximally-facing surface 121 to guide the fluid from the lumen 112 to the exit port 124. In a particular embodiment, at least a portion of the distal face 122 can be formed from the distal-most surface of the guide-member 120. Although the embodiment of FIG. 2A shows a guide-member 120 having a guide-member length GL that is less than an inner member 110 length, in other embodiments the guide-member 120 can have any suitable length, including a length GL generally equivalent to the length of the inner member 110. As shown in FIGS. 2A-2B, the guide-member 120 can be a separate component fixed to the wall 111 via adhesive, soldering, welding, etc. In other embodiments, the guide-member 120 can be integral with the wall 111. For example, during manufacturing, the wall 111 can be molded to include the guide-member 120. In other embodiments, the guide-member 120 can have other suitable shapes, sizes, and/or configurations. For example, in some embodiments, the guide-member 120 can have a generally constant thickness along its length and can extend along all or a portion of the inner member 110.

The inner member lumen 112 can have a first region 114, a second region 116, and a third region 118. The first region 114 can be defined by the portion of the lumen 112 extending between the distal-most edge 126 of the distal face 122 and the proximal-most edge 128 of the distal face 122. The second region 116 can be defined by the portion of the lumen 112 extending between the proximal-most edge 128 of the distal face 122 and a proximal terminus of the guide-member 120. The third region 118 can be defined by the portion of the inner member 110 extending between the proximal terminus of the guide-member 120 and a proximal region (not shown) of the inner member 110. Together, the first region 114, the second region 116, and the third region 118 can form the inner member lumen 112. The first region 114 can have a first average diameter, the second region 116 can have a second average diameter, and the third region 118 can have a third average diameter. The first average diameter can be less than the second average diameter, and the second average diameter can be less than the third average diameter. Although FIGS. 2A-2B show the first region 114 running generally parallel to the longitudinal axis A of the inner member 110 and having a generally constant diameter, in other embodiments, the first lumen 134 can have other suitable configurations (e.g., angled relative to the longitudinal axis A, having a varying diameter along its length, etc.). Likewise, the second and third inner diameters can be the same or different along the lengths of the second and third regions, 116, 118, respectively.

In some embodiments, the lumen 112 does not include a second region 116. For example, in some embodiments, the wall 111 can include a step increase (not shown) between the first region 114 and the third region 118 such that the length of the second region 116 is effectively zero. Additionally, in some embodiments, the lumen 112 does not include a third region 118. For example, in some embodiments, the proximal terminus of the guide-member 120 can generally align with the proximal terminus of the inner member 110. In such embodiments, the guide-member 120 can gradually taper in a proximal direction.

It will be appreciated that any of the inner member 110 embodiments described herein can be used regardless of the overall shape and/or configuration of the inner member 110. For example, all or portions of the inner member 110 can have a curved shape; in such embodiments, the inner member 110 can still include a guide-member 120, tapered lumen, etc.

II. Methods of Use

Figure 3A:
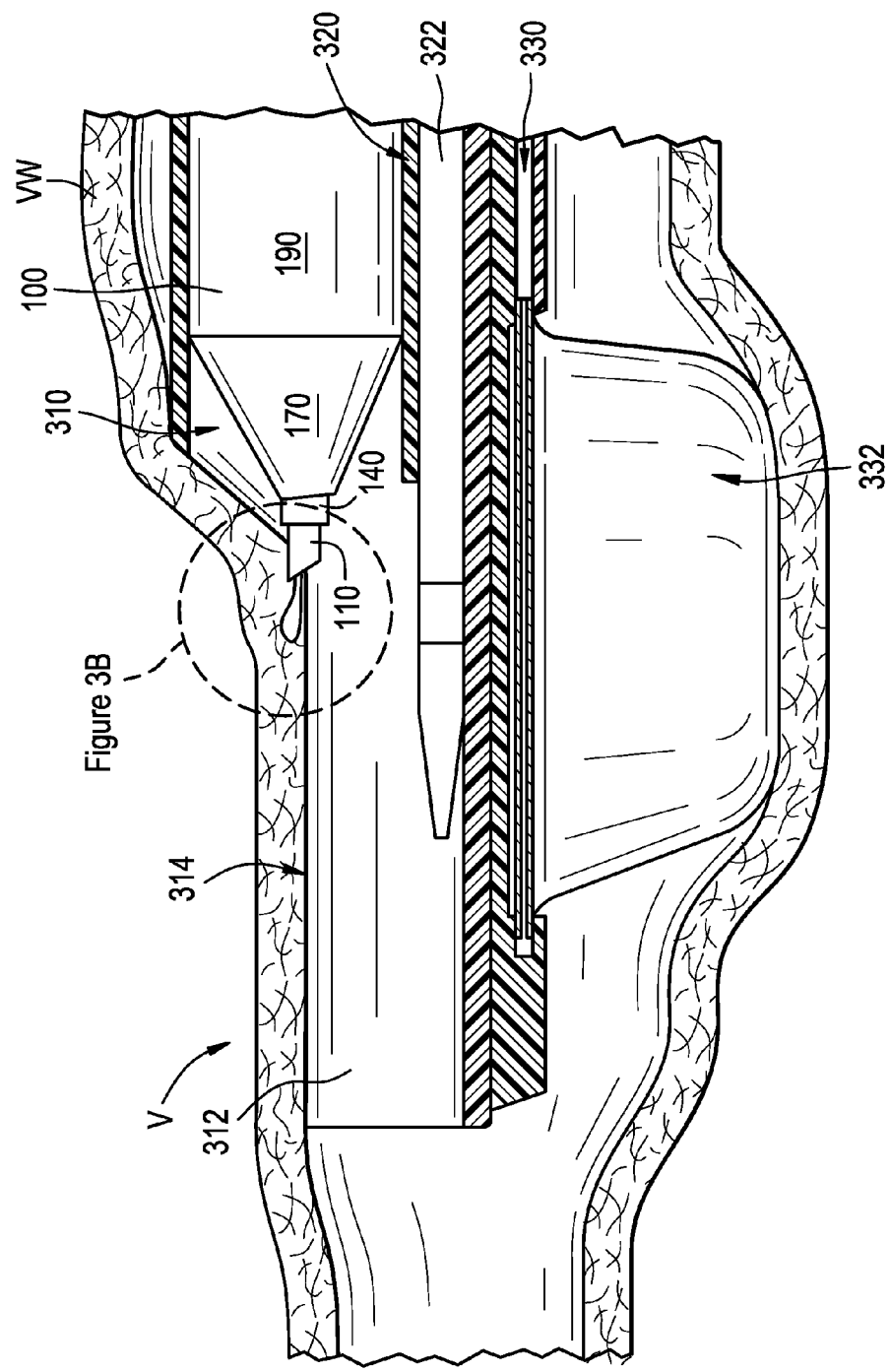

FIGS. 3A-3D illustrate one example for using the dissection assembly 100 to dissect vessel wall tissue. FIG. 3A is a side partial cross-sectional view of one embodiment of a delivery catheter 300 for delivering the dissection assembly 100 to a dissection site shown in an expanded state and positioned within a vessel V. In FIG. 3A, the delivery system 300 is shown along with the dissection assembly 100 and a visualization catheter 322. The delivery system 300 can include a dissection assembly lumen 310 configured to slidably receive the dissection assembly 100, an open trough 312 having tissue engaging portions 314, a visualization lumen 320 configured to slidably receive the visualization catheter 322, an expandable element 332, and an expansion lumen 330 coupled to the expandable element 332. In the expanded state, the trough 312 engages the vessel wall VW and stretches the wall VW across the top of the tissue engaging portions 314. This fixes the vessel wall VW tissue at a known height relative to the dissection assembly lumen 310. As such, based on the configuration of the dissection assembly 100, the inner member 110 can puncture the wall VW at a predetermined elevation along the height of the wall, as shown in FIG. 3A.

Although the delivery catheter 300 and dissection assembly 100 can work together to ensure the initial wall puncture occurs at a desired elevation and angle, hydrodissection of the vessel wall VW cannot occur until the entire exit port 124 (FIGS. 2A-2B) of the inner member 110 is within the vessel wall VW. This is because the pressurized fluid moving through the lumen 112 will take the path of least resistance; when only a portion of the exit port 124 is positioned within the vessel wall, the ejected fluid encounters a large resistance at the portion of the exit port in contact with the vessel wall tissue, and only a very small resistance at the portion of the exit port fluidly coupled to the vessel lumen. Conventional medical needles have beveled distal edges with exit ports that span the full cross-sectional dimension of the distal face of the bevel (e.g., the exit port extends from the distal tip to the proximal heel of the bevel). As such, before hydrodissection can occur with a conventional needle, the entire diameter of the needle must be positioned within the vessel wall VW. As a result, the depth of vessel wall penetration is in part dictated by the diameter of the needle. Choice of needle diameter, however, can be limiting, as the diameter of the needle affects the pushability and rigidity of the needle, as well as the pressure with which a fluid can be transferred through the needle lumen. In those medical procedures involving dissection of thin, fragile tissue, such as creating a valve leaflet from a vessel wall, it can be advantageous to reduce the depth of penetration into the vessel wall for at least the following reasons: (1) the shallower the penetration, the thicker the portion of the vessel wall left intact to support the leaflet and to maintain hemostasis in the vessel, and (2) shallow penetration results in a thin, flexible flap of tissue that better imitates the dynamic properties of a native leaflet.

The dissection assembly 100 of the present technology overcomes the drawbacks of conventional needles and provides additional advantages for dissecting vessel wall tissue. As shown in the enlarged view of the distal portion of the inner member 110 in FIG. 3B, the guide-member 120 restricts the exit port 124 opening to the distal portion of the distal face 122, thus allowing fluid to begin flowing into the vessel wall and separating tissue layers (e.g., hydrodissection) without the entire diameter of the inner member 110 being advanced into the vessel wall VW. For example, the inner member 110 can dissect the vessel wall VW at a puncture depth equal to the combined exit port diameter $d_{ep}$ and wall portion thickness $t_d$ (FIG. 2A), thus separating a thin flap F of vessel wall tissue from the vessel wall VW. For example, in some embodiments, the puncture depth can be between about ¼ to about ⅛ of the vessel wall thickness (assuming an average vessel wall thickness of about 1 mm).

Figure 3B:
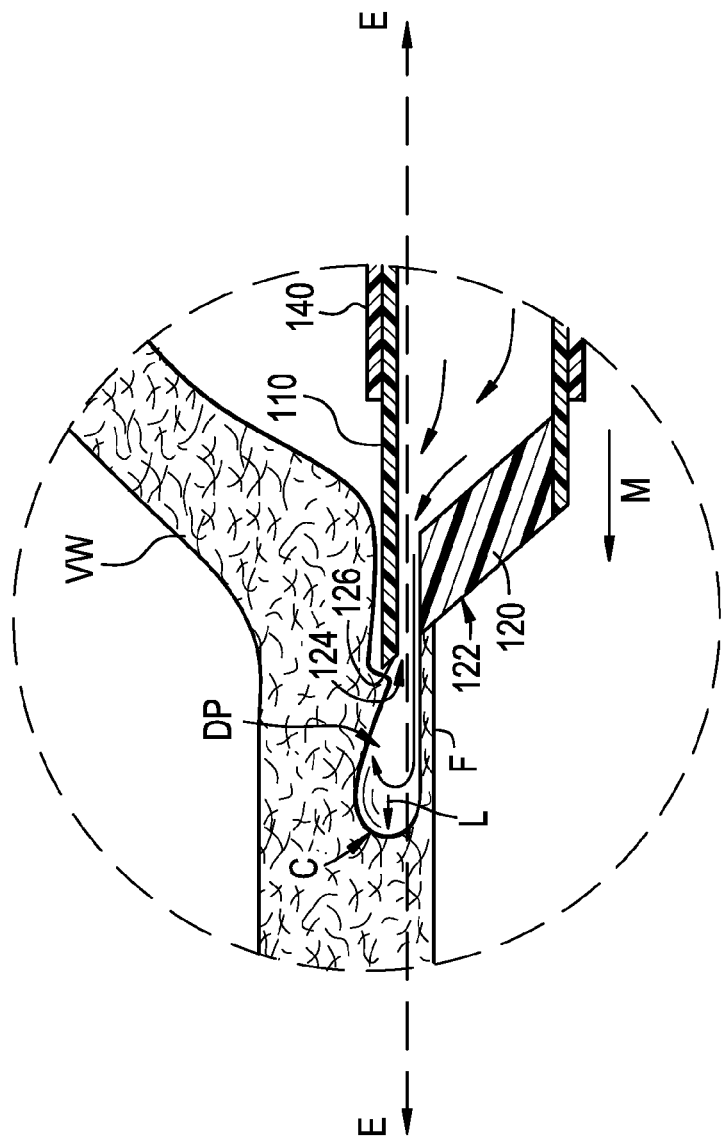
Figure 3C:
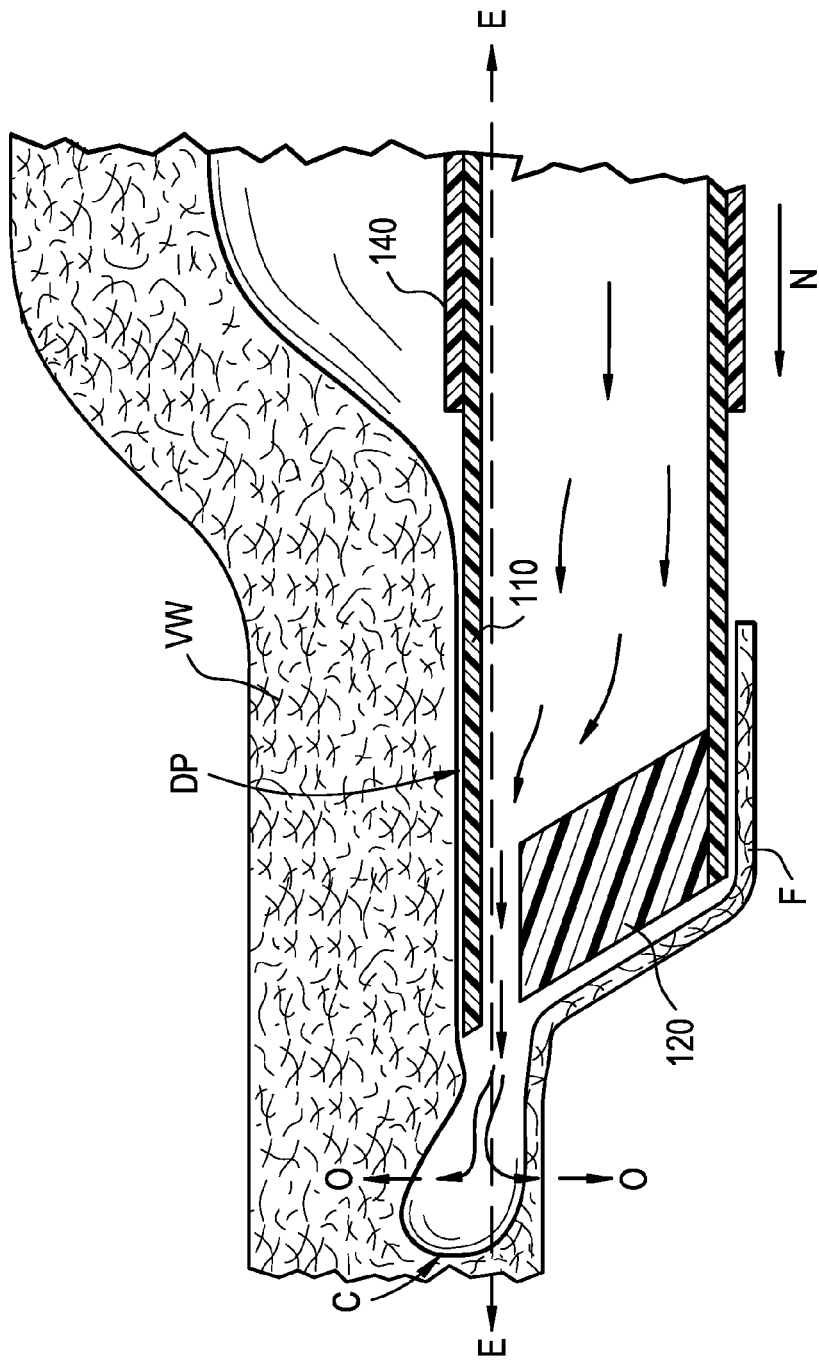

As fluid continues to flow out of the exit port 124 and into the newly created dissection pocket DP, the pressurized fluid exerts a distal force (indicated by arrow L) on a distal edge C of the dissection pocket. This distal force causes the tissue to separate at the edge C and lengthens the dissection pocket DP. Referring to FIGS. 3B-3C, as the dissection pocket DP lengthens, the length of the thin flap F of vessel wall tissue separated from the rest of the vessel wall VW also increases such that the inner member 110 can be advanced distally (indicated by arrow M in FIG. 3B) within the dissection pocket DP at the same shallow elevation E as the initial puncture, without necessarily having to contact the edge C.

Eventually, the fluid force against the distal edge C is not sufficient to continue to lengthen the dissection pocket DP. Despite the distal advancement of the inner member 110, the dissection pocket DP begins to distend radially outwardly (as indicated by arrows O in FIG. 3C, as well as a direction into and out of the page, which is not shown in the side view). At this point, the inner sheath 140 can be advanced distally over the inner member 110, as indicated by arrow N in FIG. 3C. As shown in FIG. 3D, the blunt distal face 144 of the inner sheath 140 can engage the tissue along the periphery of the dissection pocket DP and force the tissue apart at the edge C, thereby lengthening the dissection pocket DP. Moreover, distal advancement of blunt distal face 144 to a position distal of the puncturing edge 126 covers the puncturing edge 126 and protects the tissue. Depending on the procedural requirements, once the blunt distal face 144 of the inner sheath is distal of the puncturing edge 126 of the inner member 110, the inner member 110 (while ejecting fluid or not) and the inner sheath 140 can continue to be advanced simultaneously within the dissection pocket DP, the inner member 110 (while ejecting fluid or not) and the inner sheath 140 can be advanced and/or withdrawn at different rates within the dissection pocket DP, the inner member 110 can be withdrawn, and/or the inner sheath 140 can be withdrawn.

In some embodiments, the dissection assembly 100 can additionally or alternatively include an elongated member (not shown) having a rounded, blunt distal portion that can be advanced within the inner member 110 to a location such that the rounded distal portion is distal of the distal-most or puncturing edge 126 and thus protects the tissue in the dissection pocket from the puncturing edge 126.

III. Selected Embodiments of Pressure Monitoring Devices and Methods of Use

Figure 4:
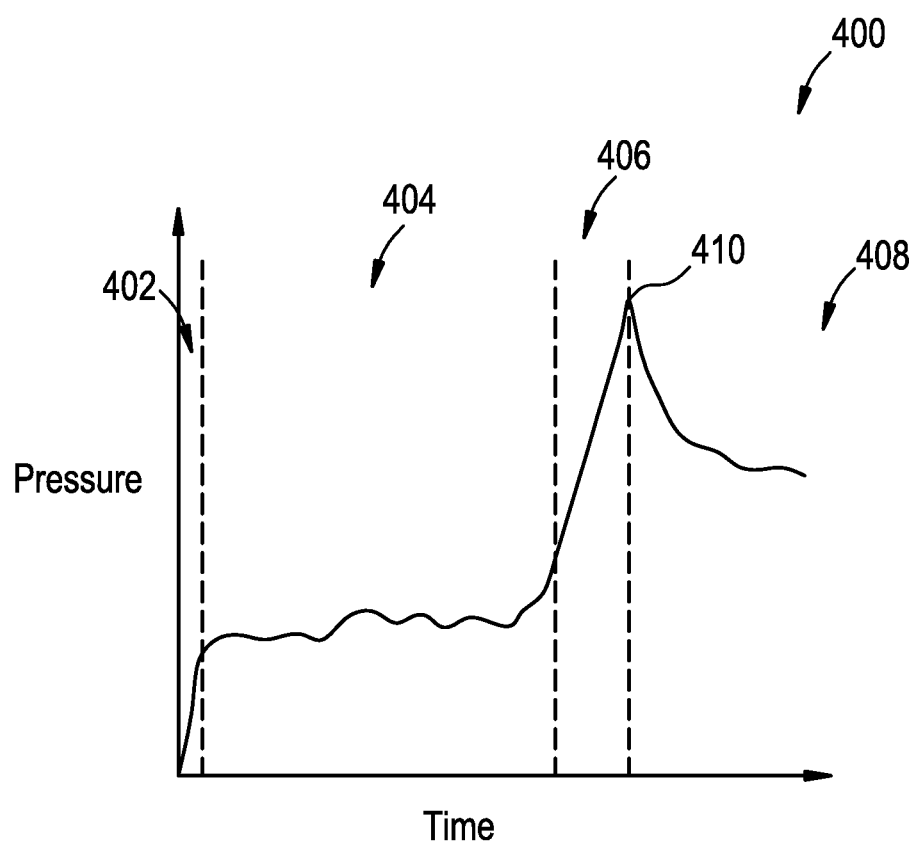
FIG. 4 is a graph showing pressure versus time during a dissection procedure in accordance with an embodiment of the present technology.

In some embodiments, the dissection assembly can further include a pressure sensor (not shown) and/or the pressurized fluid source can include a pressure sensor. The pressure sensor can indicate to the clinician the position of the inner member 110 during a dissection procedure, for example, and thus inform the clinician on dissection status. FIG. 4 is a graph showing pressure versus time during a dissection procedure. At t=0, the pressurized fluid source is coupled to the inner member 110 and activated (e.g., by depressing a plunger on a syringe, rotating a knob on an indeflator, a pump is turned on, etc.) to begin pushing fluid through the inner member lumen 112 (FIG. 2A) at a generally constant rate. As indicated by time period 402, pressure within the inner member 110 and/or fluid source immediately increases as the fluid moves through the lumen 112 towards the exit port 124. Once the fluid reaches the exit port 124 and contacts the bodily fluid (e.g., blood) present in the vessel lumen, the pressure generally stabilizes, as indicated by time period 404. At some point, the inner member 110 is advanced distally such that the distal-edge 126 contacts the vessel wall and gains entry to an interior portion of the vessel wall. As the inner member 110 is further advanced within the vessel wall, the vessel wall tissue covers a portion of the exit port 124. As a result, the pressure begins to increase, as indicated by the start of time period 406. As the inner member 110 continues to move distally, the portion of the exit port 124 covered by the vessel wall tissue increases which results in a continued increase in the monitored pressure (as shown during 406). Eventually, the inner member 110 advances distally enough that the vessel wall covers the entire cross-sectional dimension of the exit port 124. At the moment the entire cross-sectional dimension is first covered, the pressure reaches a maximum value 410. Immediately thereafter, the fluid leaving the exit port 124 exerts enough pressure on the tissue adjacent the exit port 124 to force the tissue to separate (e.g., dissection begins), thereby creating a small pocket at the exit port 124. As the tissue separates the pressure decreases, as indicated by time period 408.

The dissection assembly 100 of the present technology can include a display (not shown) that informs the clinician of the dissection status of the procedure based on the monitored pressure. Such a feature can be advantageous for several reasons. First, real-time pressure data allows the clinician to adjust the pressure of the ejected fluid as needed. For example, the clinician may choose to approach the vessel wall at a first pressure pt, but decrease the pressure to a second pressure $p_2$ once the vessel wall tissue begins to separate. Second, real-time pressure data can be one way in which the clinician tracks the size of the dissection pocket. For example, the clinician can use the pressure data to determine the position of the inner member 110 and/or inner sheath 140 at the moment hydrodissection begins (e.g., around 410), and then measure the distance inner member 110 and/or sheath 140 moves thereafter to estimate the length of the dissection pocket. Third, real-time pressure data can alert the clinician as to any abnormalities in the procedure. For example, a pressure increase 406 that is not followed by a decrease 408 in an expected amount of time can alert the clinician that the exit port 124 may be covered by a particularly fibrous or calcified portion of the vessel wall. Likewise, a decrease in pressure 408 that occurs too quickly and/or drops to a pressure value below a predetermined value can alert the clinician that the inner member 110 has pierced completely through the vessel wall or has entered back into the vessel lumen. In either scenario, the clinician could then move the delivery system to a more suitable portion of the vessel for dissection.

In some embodiments, the dissection assembly 100 and/or pressure sensor can be coupled to a console (not shown) that displays a plot of pressure versus time. In a particular embodiment, the pressure sensor can be coupled a controller (not shown) associated with the console. The controller can include memory and processing circuitry that include one or more algorithms for automatically monitoring and analyzing the pressure data. For example, the controller can monitor the real-time pressure data and look for changes in pressure and/or absolute pressure readings outside of predetermined thresholds. Based on the analysis, the controller can alert the clinician as to the status of the dissection. For example, the controller might trigger a green light to flash (not shown) on the handle or on a screen at the point of puncture. Many other potential indicators or warnings could similarly be activated by such a controller. In other embodiments, a proximal portion of the dissection assembly 100 and/or delivery catheter 300 can include a pressure gauge that displays the pressure data.

IV. Further Examples

The following examples are illustrative of several embodiments of the present technology:

1. A dissection device, comprising:
   a tubular elongated member having a lumen therethrough, wherein the elongated member includes—
      a proximal region configured to be positioned external to a human patient and a distal region configured to be intravascularly delivered to a blood vessel and positioned within a blood vessel wall, wherein the distal region includes an angled distal face having a distal-most edge configured to puncture the vessel wall and a proximal-most edge; and
      an exit port located along the distal face and in fluid communication with the lumen, wherein a central longitudinal axis of the exit port is offset from a central longitudinal axis of the elongated member such that the exit port is positioned along the distal face closer to the distal-most edge than the proximal-most edge.

2. The device of example 1, further including—
   a first distance between the central longitudinal axis of the exit port and a longitudinal axis running through the distal most-edge, the first distance being perpendicular to the central longitudinal axis of the exit port and the longitudinal axis of the distal-most edge;
   a second distance between the central longitudinal axis of the exit port and a longitudinal axis running through the proximal-most edge, the second distance being perpendicular to the central longitudinal axis of the exit port and the longitudinal axis of the proximal-most edge; and
   wherein the first distance is shorter than the second distance.

3. The device of example 2 wherein the first distance is between about 35% and about 45% of the second distance.

4. The device of any of examples 1-3 wherein the elongated member is configured to be received by a tubular sheath.

5. The device of any of examples 1-4 wherein the dissection assembly is configured to be coupled to a pressurized fluid source such that inner member is configured to eject the fluid through the exit port to separate the vessel wall into two or more portions.

6. The device of any of examples 1-5 wherein the proximal-most edge of the distal face is opposite the distal-most edge of the distal face about the circumference of the elongated member.

7. The device of any of examples 1-6 wherein the elongated member includes—
   a first lumen region having a diameter that decreases along at least a portion of its length;
   a second lumen region proximal of the first lumen region, the second lumen region having a diameter that remains generally constant along its length;
   wherein the first lumen region and the second lumen region together comprise the lumen; and
   wherein the diameter of the second lumen region is greater than an average diameter of the first lumen region.

8. The device of any of examples 1-6 wherein the elongated member includes—
   an exit port lumen region having a generally constant diameter along its length, wherein the diameter of the exit port lumen region is generally equal to a diameter of the exit port;
   a proximal lumen region proximal of the exit port lumen region, the proximal lumen region having a diameter that generally remains constant along its length;
   wherein the exit port lumen region and the proximal lumen region together comprise the lumen; and
   wherein the diameter of the proximal lumen region is greater than the diameter of the exit port lumen region.

9. The device of any of examples 1-6 wherein the elongated member includes—
   a first lumen region having a generally constant diameter along its length, wherein the diameter is generally equal to a diameter of the exit port;
   a second lumen region proximal of the first lumen region, the second lumen region having a diameter that decreases along at least a portion of its length;
   a third lumen region proximal of the second lumen region, the second lumen region having a diameter that remains generally constant along its length;
   wherein the first, second, and third lumen regions together comprise the lumen; and
   wherein the diameter of the first lumen region is less than an average diameter of the second lumen region second lumen region, and the average diameter of the second lumen region is less than an average diameter of the first lumen region.

10. The device of any of examples 1-6 wherein the exit port defines an exit port diameter, and the lumen defines an inner diameter, and wherein the lumen inner diameter and the exit port diameter are generally the same along the length of the elongated member.

11. A device for dissecting a wall of a blood vessel, the device comprising:
    an elongated tubular member having a lumen therethrough, wherein the elongated member includes—
       a proximal region configured to be positioned external to a human patient and a distal region configured to be intravascularly delivered to the blood vessel and positioned within the blood vessel wall, the distal region including a slanted distal face having a proximal-most edge, a distal-most edge opposite the proximal-most edge, and an exit port positioned along the distal face between the proximal-most edge and the distal-most edge; and
       a guide-member positioned within the lumen and forming at least a portion of the distal face, wherein the guide-member is positioned between the exit port and the proximal-most edge of the distal face such that the exit port is offset from a central longitudinal axis of the elongated member towards the distal-most edge.

12. The device of example 11 wherein the guide-member has a thickness that decreases in a proximal direction.

13. The device of example 11 or example 12 wherein the guide-member has a slanted proximal portion and a distal portion that is generally parallel to a longitudinal axis of the elongated member.

14. The device of any of examples 11-13 wherein the elongated member includes—
   a first section extending between a distal-most edge of the distal face and a proximal terminus of the guide-member, wherein the lumen has a first diameter along the first section; and
   a second section extending between the proximal terminus of the guide-member and the proximal region of the elongated member, wherein the lumen has a second diameter along the second section that is greater than the first diameter.

15. The device of any of examples 11-14 wherein the elongated member is configured to be received by a tubular sheath.

16. The device of any of examples 11-15 wherein the distal-most edge of the distal face is configured to puncture vessel wall tissue.

17. The device of any of examples 11-16 wherein the dissection assembly is configured to be coupled to a pressurized fluid source such that the inner member is configured to eject the fluid through the exit port to separate the vessel wall into two or more portions.

18. A dissection assembly for separating two or more portions of a blood vessel wall, the dissection assembly comprising:
   an elongated outer member;
   a sheath positioned within the outer member; and
   an elongated inner member positioned within the sheath, the inner member having a beveled distal portion configured to puncture the blood vessel wall and eject a fluid into the blood vessel wall, wherein the distal portion includes a distal face and an exit port positioned along the distal face, wherein the distal face has—
      a first portion extending distally from a distal-most edge of the exit port along the distal face to a distal-most edge of the distal face,
      a second portion extending proximally from a proximal-most edge of the exit port to a proximal-most edge of the distal face, and
      wherein a length of the second portion is greater than a length of the first portion.

19. The dissection assembly of example 18 wherein the outer member, the sheath, and the inner member are configured to moved axially relative to one another.

20. The dissection assembly of example 18 or example 19 wherein the outer member has a tapered distal portion configured to separate vessel wall tissue.

21. The dissection assembly of any of examples 18-20 wherein the sheath is an inner sheath, and wherein the dissection assembly further comprises an outer sheath disposed around the outer member.

22. The dissection assembly of any of examples 18-21 wherein the sheath is an inner sheath, and wherein the dissection assembly further comprises an outer sheath disposed around the outer member, the outer sheath configured to be received by a lumen of a delivery catheter.

23. A method for separating two or more portions of a vessel wall, the method comprising:
   intravascularly delivering a dissection assembly to a dissection site adjacent the vessel wall, wherein the dissection assembly includes an elongated tubular member having a slanted distal face and an exit port positioned along the distal face;
   forming an opening in the vessel wall with the elongated member;
   advancing the exit port through the opening; and
   separating vessel wall tissue by ejecting fluid through the exit port while a portion of the distal face remains outside of the opening.

24. The method of example 23, further comprising forming a dissection pocket within the vessel wall.

25. The method of example 24, further comprising lengthening the dissection pocket by advancing the elongated member distally within the dissection pocket.

26. The method of example 25 wherein advancing the elongated member distally within the dissection pocket occurs while ejecting fluid through the exit port.

27. The method of example 24 wherein the dissection assembly further comprises a sheath disposed around the elongated member, and wherein the method further comprises lengthening the dissection pocket by advancing the sheath over the elongated member such that a distal portion of the elongated member engages a periphery of the dissection pocket to force vessel wall tissue to separate at a distal edge of the dissection pocket.

28. The method of example 23 wherein forming an opening in the vessel wall occurs while ejecting fluid from the exit port.

29. The method of example 23 wherein the elongated member is an inner elongated member, and the dissection assembly further includes a sheath disposed around the inner elongated member and an outer elongated member disposed over the sheath, the method further comprising distally advancing the outer member over the sheath and through the opening.

30. The method of example 23 wherein the elongated member is an inner elongated member, and the dissection assembly further includes an inner sheath disposed around the inner elongated member, an outer elongated member disposed over the inner sheath, and an outer sheath disposed over the outer elongated member, wherein the method further comprises—
   distally advancing the outer member over the inner sheath and through the opening; and
   distally advancing the outer sheath over the outer member and through the opening.

V. Conclusion

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A method for separating two or more portions of a vessel wall, the method comprising:
   intravascularly delivering a dissection assembly to a dissection site adjacent the vessel wall, the dissection assembly including an elongated tubular member having a slanted distal face and an exit port positioned along the distal face, wherein the distal face has a distal-most edge and a proximal-most edge, and wherein a central longitudinal axis of the exit port is offset from a central longitudinal axis of the elongated tubular member such that the exit port is positioned along the distal face closer to the distal-most edge than the proximal-most edge, and wherein the elongated tubular member further includes a first distance between the central longitudinal axis of the exit port and a longitudinal axis running through the distal most-edge, the first distance being perpendicular to the central longitudinal axis of the exit port and the longitudinal axis of the distal-most edge, a second distance between the central longitudinal axis of the exit port and a longitudinal axis running through the proximal-most edge, the second distance being perpendicular to the central longitudinal axis of the exit port and the longitudinal axis of the proximal-most edge, and wherein the first distance is between about 35% and about 45% of the second distance; and forming an opening in the vessel wall with the elongated tubular member;

advancing the exit port through the opening; and separating vessel wall tissue by ejecting fluid through the exit port while a portion of the distal face remains outside of the opening.

2. The method of claim 1, further comprising forming a dissection pocket within the vessel wall.

3. The method of claim 2, further comprising lengthening the dissection pocket by advancing the elongated tubular member distally within the dissection pocket.

4. The method of claim 3 wherein advancing the elongated tubular member distally within the dissection pocket occurs while ejecting fluid through the exit port.

5. The method of claim 2 wherein the dissection assembly further comprises a sheath disposed around the elongated tubular member, and wherein the method further comprises lengthening the dissection pocket by advancing the sheath over the elongated tubular member such that a distal portion of the sheath engages a periphery of the dissection pocket to force vessel wall tissue to separate at a distal edge of the dissection pocket.

6. The method of claim 1 wherein forming an opening in the vessel wall occurs while ejecting fluid from the exit port.

7. The method of claim 1 wherein the elongated tubular member is an inner elongated member, and the dissection assembly further includes a sheath disposed around the inner elongated member and an outer elongated member disposed over the sheath, the method further comprising distally advancing the outer elongated member over the sheath and through the opening.

8. The method of claim 1 wherein the elongated tubular member is an inner elongated member, and the dissection assembly further includes an inner sheath disposed around the inner elongated member, an outer elongated member disposed over the inner sheath, and an outer sheath disposed over the outer elongated member, wherein the method further comprises— distally advancing the outer elongated member over the inner sheath and through the opening; and distally advancing the outer sheath over the outer elongated member and through the opening.

9. The method of claim 2 wherein the dissection assembly further comprises a sheath disposed around the elongated tubular member, and wherein the method further comprises:

lengthening the dissection pocket by advancing the sheath over the elongated tubular member such that a distal portion of the sheath engages a periphery of the dissection pocket to force vessel wall tissue to separate at a distal edge of the dissection pocket; and ejecting fluid from a distal end of the elongated tubular member while advancing the sheath over the elongated tubular member.

10. The method of claim 1 wherein separating vessel wall tissue by ejecting fluid through the exit port occurs while the entire exit port is within the vessel wall and a proximal portion of the distal face remains proximal of the opening.

11. The method of claim 1 wherein separating vessel wall tissue by ejecting fluid through the exit port occurs while the proximal-most edge of the distal face remains outside of the opening.

12. The method of claim 1 wherein forming the opening in the vessel wall with the elongated tubular member includes forming the opening in the vessel wall with the distal-most edge of the distal face.

13. A method for separating two or more portions of a vessel wall, the method comprising:

intravascularly delivering a dissection assembly to a dissection site adjacent the vessel wall, wherein the dissection assembly includes an elongated tubular member having a slanted distal face, an exit port positioned along the distal face, a sidewall defining a lumen, and a guide member that is a separate component fixed to the sidewall within the lumen, wherein at least a portion of the guide member is positioned at the distal face such that the guide member restricts the exit port to a distal portion of the distal face;

forming an opening in the vessel wall with the elongated tubular member;

advancing the exit port through the opening; and separating vessel wall tissue by ejecting fluid through the exit port while a proximal portion of the distal face remains outside of the opening.

14. The method of claim 13 wherein the elongated tubular member includes a sidewall defining a lumen, and wherein at least a portion of the guide member is positioned within the lumen.

15. The method of claim 13 wherein the guide member extends along only a portion of the elongated tubular member.

16. The method of claim 13 wherein the guide member extends along the entire length of the elongated tubular member.

17. The method of claim 13 wherein forming the opening in the vessel wall with the elongated tubular member includes forming the opening in the vessel wall with a distal-most edge of the distal face.

18. The method of claim 13, further comprising forming a dissection pocket within the vessel wall.

19. The method of claim 18, further comprising lengthening the dissection pocket by advancing the elongated tubular member distally within the dissection pocket.

20. The method of claim 19 wherein advancing the elongated tubular member distally within the dissection pocket occurs while ejecting fluid through the exit port.

21. The method of claim 18 wherein the dissection assembly further comprises a sheath disposed around the elongated tubular member, and wherein the method further comprises lengthening the dissection pocket by advancing the sheath over the elongated tubular member such that a distal portion of the sheath engages a periphery of the dissection pocket to force vessel wall tissue to separate at a distal edge of the dissection pocket.

22. The method of claim 18 wherein the dissection assembly further comprises a sheath disposed around the elongated tubular member, and wherein the method further comprises:

lengthening the dissection pocket by advancing the sheath over the elongated tubular member such that a distal portion of the sheath engages a periphery of the dissection pocket to force vessel wall tissue to separate at a distal edge of the dissection pocket; and ejecting fluid from a distal end of the elongated tubular member while advancing the sheath over the elongated tubular member.

23. A method for separating two or more portions of a vessel wall, the method comprising:
   intravascularly delivering a dissection assembly to a dissection site adjacent the vessel wall, wherein the dissection assembly includes an elongated tubular member having a slanted distal face, an exit port positioned along the distal face, a sidewall defining a lumen, and a guide member, wherein (1) at least a portion of the guide member is positioned at the distal face such that the guide member restricts the exit port to a distal portion of the distal face, and (2) at least a portion of the guide member is positioned within the lumen and has a ramped, proximally-facing surface;
   forming an opening in the vessel wall with the elongated tubular member;
   advancing the exit port through the opening; and
   separating vessel wall tissue by ejecting fluid through the exit port while a proximal portion of the distal face remains outside of the opening.

* * * * *